(12) United States Patent
Hibbard

(10) Patent No.: US 6,249,594 B1
(45) Date of Patent: Jun. 19, 2001

(54) AUTOSEGMENTATION/AUTOCONTOURING SYSTEM AND METHOD

(75) Inventor: Lyn Hibbard, St. Louis, MO (US)

(73) Assignee: Computerized Medical Systems, Inc., St. Louis, MO (US)

(*) Notice: Subject to any disclaimer, the term of this patent is extended or adjusted under 35 U.S.C. 154(b) by 0 days.

(21) Appl. No.: 09/087,254

(22) Filed: May 29, 1998

Related U.S. Application Data

(63) Continuation-in-part of application No. 08/813,701, filed on Mar. 7, 1997, now Pat. No. 5,859,891.

(51) Int. Cl.$^7$ .................................................. G06K 9/00
(52) U.S. Cl. ............................................................ 382/128
(58) Field of Search ................................... 382/128, 130, 382/199, 173, 180, 155, 159, 256; 128/922

(56) References Cited

U.S. PATENT DOCUMENTS

| | | | |
|---|---|---|---|
| 4,751,643 | 6/1988 | Lorensen et al. | 364/414 |
| 4,764,971 | 8/1988 | Sullivan | 382/9 |
| 4,791,567 | 12/1988 | Cline et al. | 364/413.13 |

(List continued on next page.)

FOREIGN PATENT DOCUMENTS

| | | | |
|---|---|---|---|
| 0 424 912 | 10/1990 | (EP) | 15/68 |
| 96/42070 | 12/1996 | (WO) | G06T/5/00 |

OTHER PUBLICATIONS

Fletcher et al., A Multispectral Analysis of Brain Tissues, *Magnetic Resonance in Medicine*, vol. 29, pp. 623–630 (1993).

Miller et al., Mathematical Textbook of Deformable Neuroanatomies, Proceedings of the National Academy of Sciences USA, vol. 90, pp. 11944–11948 (1993).

Staib et al., Boundary Finding with Parametrically Deformable Models, *IEEE Transactions on Pattern Analysis and Machine Intelligence*, vol. 14, pp. 859–870 (1996).

Chakraborty et al., Deformable Boundary Finding in Medical Images by Integrating Gradient and Region Information, *IEEE Transactions on Medical Imaging*, vol. 15, pp. 859–870 (1996).

(List continued on next page.)

*Primary Examiner*—Andrew W. Johns
*Assistant Examiner*—Shervin Nakhjavan
(74) *Attorney, Agent, or Firm*—Hale and Dorr LLP

(57) ABSTRACT

A system and method is disclosed for automatically computing contours representing the boundaries of objects in three-dimensional tomographic images that may be formed by computed tomography ("CT"), magnetic resonance imaging ("MRI"), positron emission tomography ("PET"), single proton emission computed tomography ("SPECT"), or other appropriate methods. The system and method begin with a sample region of the object's interior and the single region is expanded in a step-wise fashion. At each step, a contour maximally matching the region's current edge, local gray-level gradient maxima, and prior contour shapes is determined. Upon completion of region expansion, the object contour is set to that step-contour having the maximum value of an objective function summing contributions from region edges, gradient edges, and prior shapes. Both the region expansion and the boundary contour determination are formulated such that there is a guaranteed average minimum error in the determination of the contours. This contour is represented as a parametric curve in which the contour size and shape are specified by the values of the parameters. These parameters are independent variables of the objective function. The parameters also are considered to be random variables capable of encoding a distribution of contour shapes, and by assuming a particular distribution, the contribution of shape constraints to the object function can be computed. The resulting contour corresponds to the set of parameters for which the objective function is a maximum.

22 Claims, 6 Drawing Sheets

U.S. PATENT DOCUMENTS

| | | | |
|---|---|---|---|
| 4,856,074 | 8/1989 | Nagaoka | 382/22 |
| 4,961,425 | 10/1990 | Kennedy et al. | 128/653 R |
| 5,133,020 | 7/1992 | Giger et al. | 382/6 |
| 5,166,876 | 11/1992 | Cline et al. | 364/413.13 |
| 5,185,809 | 2/1993 | Kennedy et al. | 382/6 |
| 5,187,658 | 2/1993 | Cline et al. | 364/413.13 |
| 5,204,625 | 4/1993 | Cline et al. | 324/306 |
| 5,239,591 | 8/1993 | Ranganath | 382/6 |
| 5,289,374 | 2/1994 | Doi et al. | 364/413.13 |
| 5,319,549 | 6/1994 | Katsuragawa et al. | 364/413.13 |
| 5,319,551 * | 6/1994 | Sekiguchi et al. | 364/413.19 |
| 5,371,810 * | 12/1994 | Vaidyanathan | 382/291 |
| 5,410,617 | 4/1995 | Kidd et al. | 382/51 |
| 5,412,563 | 5/1995 | Cline et al. | 364/413.22 |
| 5,433,199 | 7/1995 | Cline et al. | 128/653.1 |
| 5,452,367 | 9/1995 | Bick et al. | 382/128 |
| 5,457,754 | 10/1995 | Han et al. | 382/128 |
| 5,458,126 | 10/1995 | Cline et al. | 128/653.1 |
| 5,491,627 | 2/1996 | Zhang et al. | 364/413.2 |
| 5,517,602 | 5/1996 | Natarajan | 395/119 |
| 5,531,223 | 7/1996 | Hatanaka | 128/653.2 |
| 5,537,485 | 7/1996 | Nishikawa et al. | 382/130 |
| 5,566,246 | 10/1996 | Rao | 382/154 |
| 5,570,430 | 10/1996 | Sheehan et al. | 382/128 |
| 5,574,799 | 11/1996 | Bankman et al. | 382/132 |
| 5,583,659 | 12/1996 | Lee et al. | 358/455 |
| 5,590,215 | 12/1996 | Allen | 382/128 |
| 5,669,382 | 9/1997 | Curwen et al. | 128/653.1 |
| 5,734,739 | 3/1998 | Sheehan et al. | 382/128 |
| 5,974,165 * | 10/1999 | Giger et al. | 382/132 |

OTHER PUBLICATIONS

McInerney et al., Deformable Models in Medical Image Analysis, *Proceedings of Mathematical Methods Biomedical Image Analysis*, pp. 171–180 (1996).

Giardina et al., Accuracy of Curve Approximation by Harmonically Related Vectors with Elliptical Loci, *Computer Graphics and Image Processing*, vol. 6, pp. 277–285 (1977).

Kuhl et al., Elliptic Fourier Features of a Closed Contour, *Computer Graphics and Image Processing*, vol. 18, pp. 236–258 (1982).

Wells et al., Adaptive Segmentation of MRI Data, *IEEE Transactions on Medical Imaging*, vol. 15, No. 4, pp. 429–442 (1996).

Cline et al.; Three–Dimensional Segmentation of MR Images of the Head using Probability and Connectivity; (1990); *Journal of Computer Assisted Tomography*, vol. 14(6): pp. 1037–1045.

Cline et al.; 3D Reconstruction of the Brain from Magnetic Resonance Images using a Connectivity Algorithm; (1987); *Magnetic Resonance Imaging*, vol. 5: pp. 345–352.

Cline et al.; Vascular Morphology by Three–Dimensional Magnetic Resonance Imaging; (1989); *Magnetic Resonance Imaging*, vol. 7: pp. 45–54.

Bezdek et al.; Review of MR Image Segmentation Techniques using Pattern Recognition; (1993); *Medical Physics*, vol. 20(4): pp. 1033–1048.

DeCarli et al.; Method for Quantification of Brain, Ventricular, and Subarachnoid CSF Volumes from MR Images; (1992); *Journal of Computer Assisted Tomography*, vol. 16(2): pp. 274–284.

Höhne et al.; Interactive 3d Segmentation of MRI and CT Volumes using Morphological Operations; (1992); *Journal of Computer Assisted Tomography*, vol. 16(2): pp. 285–294.

Kohn et al.; Analysis of Brain and Cerebrospinal Fluid Volumes with MR Imaging; (1991); *Radiology*, vol. 178: pp. 115–122.

Neal et al.; Technical Note: Evaluation of a Region Growing Algorithm for Segmenting Pelvic Computed Tomography Images During Radiotherapy Planning; (1994); *The British Journal of Radiology*, vol. 67: pp. 392–395.

Yin et al.; Comparison of Bilateral–Subtraction and Single–Image Processing Techniques in the Computerized Detection of Mammographic Masses; (1993); *Investigative Radiology*, vol. 28(6): pp. 473–481.

Vaidyanathan et al.; Comparison of Supervised MRI Segmentation Methods for Tumor Volume Determination During Therapy: (1995); *Magnetic Resonance Imaging*, vol. 13(5): pp. 719–728.

Delagnes et al., Active Contours Approach to Object Tracking in Image Sequences with Complex Background, *Pattern Recognition Letters*, vol. 16(2), pp. 171–178 (1995).

* cited by examiner

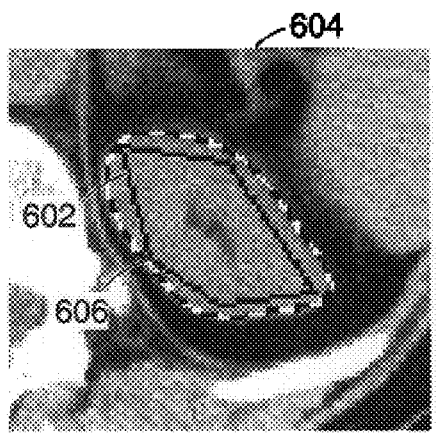
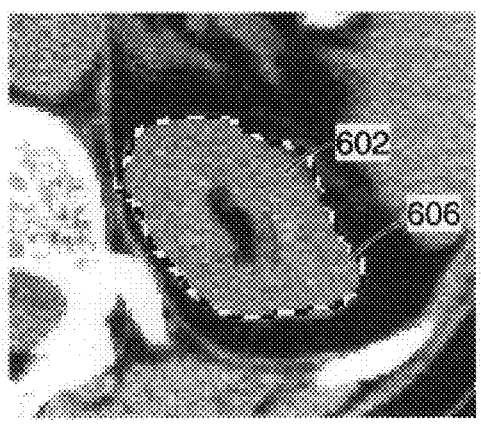
FIG. 6a　　　　　　　　FIG. 6b
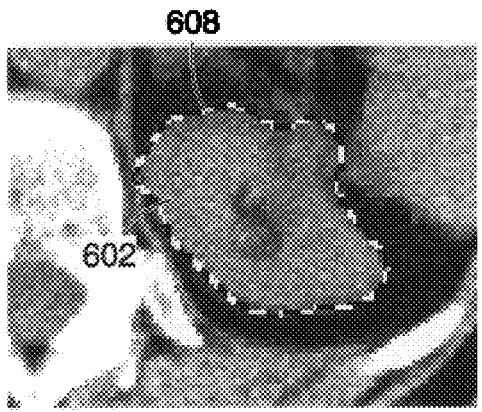
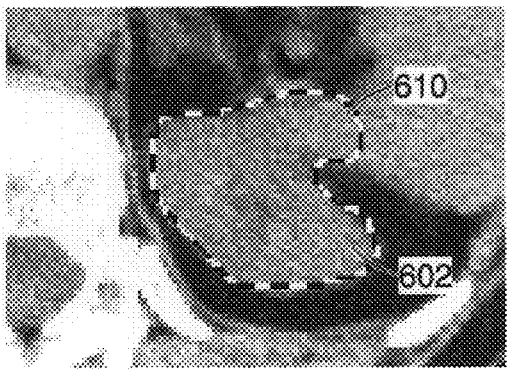
FIG. 6c　　　　　　　　FIG. 6d
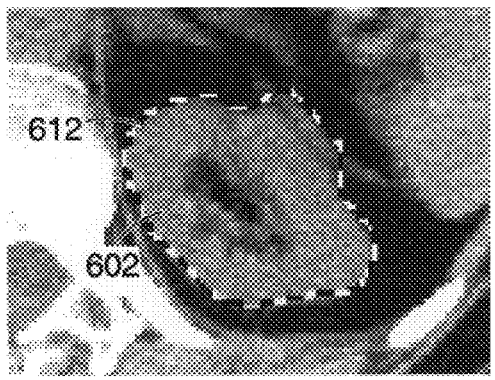
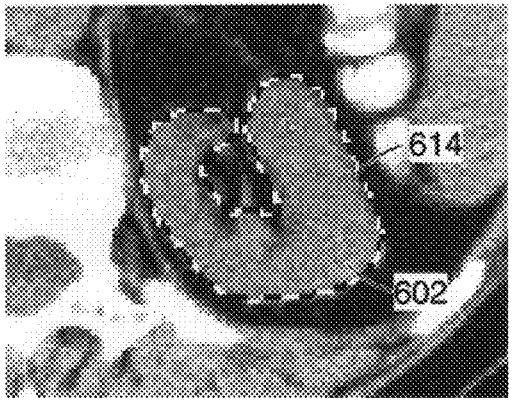
FIG. 6e　　　　　　　　FIG. 6f

AUTOSEGMENTATION/AUTOCONTOURING SYSTEM AND METHOD

RELATED APPLICATIONS

This is a continuation-in-part of U.S. patent application Ser. No. 08/813,701, filed Mar. 7, 1997, now U.S. Pat. No. 5,859,891.

FIELD OF THE INVENTION

The present invention relates to systems and methods for automatically inferring boundary contours of organs, tumors, prostheses, or other objects of medical interest from two-dimensional and three-dimensional images of the physical patient anatomy from computed tomography imaging, magnetic resonance imaging, or the like.

BACKGROUND OF THE INVENTION

Clinical Imperatives and Issues

Often in the course of clinical diagnosis, the patient's internal anatomy is imaged to determine the extent to which disease has progressed. The diseased tissue may be evidenced by some variance from normal anatomy or function. Several imaging modalities are commonly used to generate pictures (or images) of a patient's anatomy and function suitable for diagnostic and radiotherapy treatment purposes, or for surgical planning. These include conventional X-ray plane film radiography; computed tomography ("CT") imaging, which also uses X-rays, magnetic resonance imaging ("MRI"), which produces images of internal anatomy and information about physiological function; and nuclear medicine imaging techniques, such as positron emission tomography ("PET") and single photon emission computed tomography ("SPECT"), which produce images with combined anatomic and physiologic or biochemical information.

A common property shared by all the imaging modalities just mentioned is that the images are digital. That is, the images are represented as regular arrays of numerical values, which represents a physical measurement produced by a scanner. If these images are two-dimensional ("2-D"), the discrete picture elements are termed pixels. However, if the images are three-dimensional ("3-D"), the discrete volume elements are termed voxels. For 3-D imaging modalities, single slices or sections are composed of pixels, but those same picture elements are equivalently termed voxels when considering a set of stacked images as a volume of data.

The digital images from 2-D or 3-D imaging modalities are substantially exact maps of the pictured anatomy, so that each pixel value represents a sample of a property at a location in the scanner's, and, therefore, patient's, coordinate system. Thus, the distances between pixel/voxel centers are proportional and have meaning in the sense of real physical spacing in the patient anatomy. Moreover, the relative positioning of the numerical array represents the proportional spacing of objects in the patient anatomy.

The numeric value of each pixel represents a sample of a property at that location. In CT images, for example, the numbers are a measure of relative X-ray absorbing power, so that spaces inside the lungs are usually pictured as dark (low CT number) while bone is generally bright (high CT number).

CT imaging and MRI are two of the most frequently used imaging modalities because both provide detailed pictures of the internal anatomy of a patient. The instruments that employ these imaging techniques provide data that in appearance is 2-D or 3-D. However, the 3-D images, as stated, are a collection of 2-D samples, in this form of slices or sections, of the anatomy that have been combined to create a 3-D images. More specifically, to recreate the 3-D images from the 2-D image samples, the physician, scientist, or other skilled professional must recombine the 2-D image samples (slices or sections) of the anatomic elements (organs, tumors, surgically-implanted prostheses, etc.) A common way to recombine 2-D image samples to form 3-D images is to manually draw individual contours on a contiguous set of 2-D image slices or sections using computer graphics. Once these manually drawn contours are made, they are assembled to accurately construct 3-D representations of organs, tumors, and the like. The resulting 3-D reconstructions convey to the viewer the relative sizes, shapes, and mutual spatial relationships among the anatomic elements in the same anatomical scale as the original.

In the 2-D context of a slice or section, the individual anatomic elements may be represented by contours coinciding with each object's boundaries. Alternatively, in the 2-D context of a slice or section, anatomy elements may be represented by 2-D templates identical in size and shape to the object 2-D templates are patterns of pixels all having the same value which represent a single region in an image. A representation by 2-D region-templates or by 2-D edge-contours are equivalent, since either representation can be readily computed from the other.

As stated, 3-D reconstructions of patient anatomy are most often prepared using computer graphics by manually drawing the individual contours on a contiguous set 2-D image slices or sections and then combining them. This method is referred to as contouring. Contouring is very time-consuming and labor intensive. The time and labor necessary to use this method increases significantly with the number of image slices, and the number and sizes of the organs, tumors, etc. in the anatomical area of interest. The quality of the contouring and the later produced 3-D images, depend on the resolution and contrast of the 2-D images, and on the knowledge and judgment of the physician, scientist, or skilled professional performing the reconstruction.

Three-dimensional radiation therapy treatment planning ("RTTP") is a medical procedure that currently makes the greatest use of 3-D reconstructions. This is even despite the labor and time required to contour the organs and tumors to generate a useful plan. In fact, the largest fraction of the plan preparation time involves contouring.

An example of a manually contoured CT image slice or section is shown in FIG. 1 generally at 100. In FIG. 1, the manually contoured organs are liver 102, spleen 104, left kidney 106, right kidney 108, and spinal cord 110.

FIG. 2, at 200, shows an example of a 3-D reconstruction that uses as an element the 2-D slice or section shown in FIG. 1 at 100. The reconstruction in FIG. 2 is composed of contours from a contiguous set of slices or sections. In FIG. 2, the 3-D reconstruction of the liver is at 202, the spleen is at 204, the right kidney is at 206, the left kidney is at 208, and the spinal cord is at 210.

Another method that may be used for forming representations of organs, tumors, and the like is the segmentation method. Segmentation is the identification of image objects as distinct regions or segments of an image. This method also may be used to generate 3-D reconstructions of a patient's anatomy.

According to the segmentation method, a decision is made with regard to the image contents as to whether a given pixel of a 2-D slice or section belongs to a specific set of organs, tumors, lesions, or other objects known to exist in that slice or section. Therefore, given that both contouring and segmentation may equally be used to generate 3-D reconstructions, contouring and segmentation are taken to have the same meaning for description purposes herein.

Pixel/voxel values, which exist as intensities or gray levels, and their distributions across an image form a useful set of properties for segmentation. In a typical slice or section, the edges of objects that are shown usually are associated with large value differences with nearby pixel values. Further, the interiors of discrete objects tend to have relatively constant values. As such, discrete objects exhibit distinct gray level textures in such a manner that adjoining objects or regions with different textures appear to have visible boundaries between them. Each of these qualities of edgeness and texture are associated with one or more computational methods that may be used to generate a numerical value for that property. As quantified, these properties can be used to make decisions about the segment identity of individual pixels.

Prior Art Segmentation

A number of autosegmentation methods have been proposed in the prior art. These prior art methods may be separated into two principal types: (1) semi-automated segmentation methods in which physicians, technicians, or skilled professionals direct or provide some needed information which is used to produce detailed contours, and (2) fully automated segmentation methods in which a computer based program develops the segmentation without requiring any human intervention. These methods will be described in greater detail subsequently.

a. Semi-Automated Segmentation Methods

A known semi-automated method is reported in Cline, H. E., Lorensen, W. E., Kikinis, R., and Jolesz, F., *Three-dimensional segmentation of MRI images of the head using probability and connectivity, Journal of Computer Assisted Tomography,* 14:1037–1045, 1990. This method also is disclosed in whole, or in part, in U.S. Pat. No. 4,751,643 issued to Lorensen, et al. and U.S. Pat. No. 4,791,567 issued to Cline, et al.

According to this semi-automated segmentation method, the operator selects image pixels from distinct tissue in each of two or more multi-modal MRI image sets. The computer-based program then computes class conditional probability density parameters based on the assumption of a multivariate, Gaussian distribution data model. From seed pixels, the various tissues elements are grown outward by setting adjacent voxel labels according to a maximum likelihood decision rule. The labeling process is carried out over the 3-D data of the multi-modal MRI image set, followed by smoothing of the segmented region boundaries to reduce noise.

Another semi-automated approach is reported in Kohn, M. I., Tanna, N. K., Herman, G. T., et al., *Analysis of brain and cerebrospinal fluid volumes with MR imaging, Radiology,* 178:115–122 (1991). According to this approach, manually-guided segmentation of the feature space leads to image-space segmentation used to measure brain and cerebrospinal fluid volumes in MRI images.

Yet another semi-automated approach is reported in Hohne, K. H. and Hanson, W. A., *Interactive 3D segmentation of MRI and CT volumes using morphological operations, Journal of Computer Assisted Tomography,* 16(2):285–294, 1992. Following this approach, interactive gray level thresholding, and morphological erosion and dilation operations are used to more sharply define the apparent folds of the brain surface in 3-D graphics.

A semi-automated segmentation method is reported in DeCarli, C., Maisog, J., Murphy, D. G. M., et al., *Method for quantification of brain, ventricular, and subarachnoid CSF volumes from MRI images, Journal of Computer Assisted Tomography,* 16(2):274–284 (1992). This approach is directed to segmentation of major brain regions, e.g., the cerebral cortical hemispheres, cerebellum, etc., based on an analysis of gray level histograms derived from manual samples of pixel values corresponding to respective brain tissue types.

Another semi-automated segmentation method is disclosed in Neal, A. J., Sivewright, G., and Bentley, R., *Technical note: Evaluation of a region growing algorithm for segmenting pelvic computed tomography images during radiotherapy planning, British Journal of Radiology,* 67:392–395 (1994). The disclosed method is a region-growing segmentation approach. According to this approach, pixels adjacent to pixels in an initial patch centered on a graphics cursor are added to the initial patch if the gray level of the pixel is within one standard deviation of the gray level mean of the initial patch.

The semi-automated approaches that have been described all rely on two assumptions about objects in the images: 1) the pixel value means and variances are at least approximately constant throughout the object, which means that the object has statistical homogeneity, and 2) the neighboring objects have significantly different pixel value means, variances, or gray level distributions, which gives rise to visually-evident boundaries. However, problems can arise if these two assumptions are relied on too heavily because in both CT and MRI imaging in which anatomic structure contouring is preformed, the two assumptions are frequently violated. Therefore, computer-based programs dependent on regional statistical homogeneity and/or high-contrast boundaries are likely to perform very poorly.

b. Fully Automated Segmentation Methods

Fully automated, computed segmentation has been reported only for limited anatomic locations and/or narrowly-defined imaging protocols. In fully automated, computed segmentation system, an imaging modality is used to produce the original images. Modalities such as MRI are preferred because they produce images of soft tissue and display neighboring organs at higher contrast than X-ray based imaging. Further, MRI scanners can be set to produce images emphasizing proton density or different relaxation phenomena. Further, multi-modal MRI, in principle, can provide more information for each voxel.

The few fully automated, computed segmentation techniques that have been reported have been directed to the segmentation of the brain gray matter, white matter, and cerebrospinal fluid ("CSF") spaces using multi-modality MRI. These approaches use statistical pattern recognition methods to distinguish the various materials. The main fully automated computed segmentation techniques using multi-modal MRI are disclosed and described in Bezdek, J. C., Hall, L. O., Clarke, LP, *Review of MR image segmentation techniques using pattern recognition, Medical Physics,* 20:1033–1048 (1993); Fletcher, L. M., Barsotti, J. B., and Hornak, J. P., *A multispectral analysis of brain tissues, Magnetic Resonance in Medicine,* 29:623–630 (1993); Vaidyanathan, M., Clarke, L. P., Velhuizen, R. P, et al., *Comparison of supervised MRI segmentation methods for tumor volume determination during therapy, Magnetic Resonance Imaging,* 13:719–728 (1995).

A different strategy for fully automated, computed segmentation is to map a labeled atlas onto patient data by nonlinear transformations, referred to as warping. This technique will produce local correspondences between the atlas and individual patient anatomies despite inter-subject anatomic differences. An example of this strategy is reported in Miller MI, Christensen, G. E., Amit, Y., Grenander, U., *Mathematical textbook of deformable neuroanatomies, Proceedings of the National Academy of Sciences USA*, 90:11944–11948 (1993). The Miller et al. article describes a procedure in which an elastic model of the brain anatomy is driven by data-overlap probabilities to warp brain atlas images onto MRI slice or section images. In this case, segmentation occurs by associating the image voxels with atlas tissue-type labels.

Another example of a fully automated, computed segmentation method is described in Staib, L. H. and Duncan, J. S., *Boundary finding with parametrically deformable models, IEEE Transactions on Pattern Analysis and Machine Intelligence*, 14:1061–1075 (1992). According to this method, deformable models are used to segment MRI image data. U.S. Pat. No. 5,669,382 to Curwen et al., also describes this process.

A further example of a fully automated, computed segmentation method is described in Chakraborty, A., Staib, L. H., Duncan, J. S., *Deformable boundary finding in medical images by integrating gradient and region information, IEEE Transaction on Medical Imaging*, 15:859–870 (1996). The method set forth in the Chakraborty et al. article is directed to acquiring images of the left ventricle at intervals in the cardiac cycle which are then used to construct 3-D models of the left ventricle to study cardiac function.

The prior art discusses many other examples of deformable models that are used for segmentation. Many of these examples are discussed in the review of such technology in McInerney, T. and Terzoploulos, D., *Deformable models in medical image analysis*, in *Mathematical Methods Biomedical Image Analysis*, pp. 171–180 (1996).

Wells, W. M. III, Grimson, W. E. L., Kikinis, R., et al., *Adoptive segmentation of MRI data, IEEE Transactions Medical Imaging*, 15:429–442 (1996) discusses another fully automated, computed segmentation approach. According to Wells et al., there is simultaneous segmentation of the brain and CSF in MRI, and simultaneous correction of spatially-varying MR signal inhomogeneities using the knowledge of tissue intensity properties and intensity inhomogeneities. An expectation-maximization (EM) algorithm is used to compute the segmentation on the corrected intensities leading to the classification of gray and white matter in quite distorted images.

Some of the fully automated, computed segmentation methods that have just been described have experienced some success in very specific imaging modalities or anatomic settings, which have generally been the brain. The extent that these methods have found success over wider anatomic settings has depended on access to, and use of, supercomputers to compute solutions. Frequently, these methods must incorporate explicit anatomic knowledge, or knowledge of the image formation process. The ability of these methods to segment a number of different types of tissue in images having variable qualities, on single processor computers, has yet to be demonstrated.

SUMMARY OF THE INVENTION

The present invention is an autocontouring/ autosegmentation system and method for automatically computing contours representative of the boundaries of anatomical objects in two-dimensional ("2-D") and three-dimensional ("3-D") tomographic images generated using computed tomography ("CT") magnetic resonance imaging ("MRI"), positron emission tomography ("PET"), single photon emission computed tomography ("SPECT"), or other appropriate method. The system and method are useful for determining the boundary contours of an object in multiple sections of a 3-D tomographic image in a novel way. The contours generated according to the system and method of the present invention optimally match (1) local image gray level gradients, (2) the edges of the segmented object, and (3) the prior contour shape of the object at issue. These contours substantially conform to anatomic shapes with greater accuracy than hand-drawn contours.

The system and method of the present invention provide an objective method for contour construction based on quantitative measurements of properties of the images themselves. More specifically, the system and method of the present invention combines region, edge, and shape information to provide more accurate contours than methods using either region-growing or active contour approaches alone, such as reported in Chakraborty, A., Staib, L. H., Duncan, J. S., *Deformable boundary finding in medical images by integrating gradient and region information, IEEE Transactions on Medical Imaging*, 15:859–870 (1996). Further, the system and method of the present invention produce accurate contours in many anatomic sites, in images of variable quality, and require user interaction only to generate the first contour of an object.

According to the present invention, the contours that are generated are closed parametric curves such that the (x,y) coordinates of points on the curve are themselves continuous functions of arc-length t and the set of real-valued parameters, p, as provided for in Expression (1):

$$(x,y) = (x(p,t), y(p,t)) \qquad (1)$$

where, (x,y)=the Cartesian coordinates of a point on a curve.

t=the arc-length distance of a point (x,y) from an origin point.

p=a set or vector of real-value parameters.

x(p,t)=the x coordinate based on parameters p and arc-length distance t.

y(p,t)=the y coordinate based on parameters p and arc-length t.

The functions that define (x,y) will generate curves of arbitrary shape and size depending on the values of the parameters p. The parameters p serve as independent variables of an objective function which takes on greater or lesser values depending on the correlation of the computed, parametric contour and the actual object boundary in the image.

The objective function that has been referred to is determined by the sum of functions of the a posteriori conditional probabilities of the computed, parametric contour given: (1) the quality of the match of the computed boundary with the perimeter of the interior region of the actual object, (2) the coincidence of the boundary with the local gray level gradient maxima, and (3) the similarity of the shapes of the estimated boundary with previously-determined, section boundaries of the actual object.

The objective function is based on a Bayesian formulation to insure that the maximum a posteriori (MAP) result will be associated with the minimum average error in the contour determinations The formulation of the objective function as a function of a posteriori probabilities follows what is set forth in Chakraborty, A., Staib, L. H., Duncan, J. S., *Deformable boundary finding in medical images by integrating gradient and region information, IEEE Transactions on Medical Imaging*, 15:859–870 (1996) which thereby becomes part of the segmentation and method of the present invention. This maximized objective function is in the form $M(p,I_g,I_r)$, where, p is the set of real-value parameters, $I_g$ is the gray-level gradient image, and $I_r$ is the region-classified image.

In order to generate a contour according to the method of the present invention, the method initially requires a sample of the interior of the object to be contoured, called the region-of-interest ("ROI"), which is obtained either by automated comparison with a neighboring section previously contoured by this method, or by manual input using interactive computer graphics. The system and method of the present invention then expands the ROI in a stepwise fashion by: (1) adding one layer of pixels where possible to the region's perimeter, (2) renumerating the perimeter, and (3) determining the set of parameters which maximally satisfy the three criteria above. Expansion continues in this manner to an appropriate stopping point. Once this is done, the object contour is defined by the set of parameters corresponding to the maximum value of the objective function over all the expansion steps.

The expansion or growing of the ROI according to the present invention is accomplished by testing image pixels outside the region, but adjacent to the region's perimeter. The decision whether a pixel being tested belongs inside or outside of the region is made by a supervised classifier decision method. This method computes the values of discriminant functions (one each for each possible outcome) and chooses the outcome corresponding the highest valued discriminant function. The discriminant function is characterized by the assumption that the pixel gray level properties form multivariate Gaussian probability distributions. This supervised classifier decision method is developed de novo for each ROI for each section of each object. The values of the discriminant functions are set by the values of pixel gray-level properties and an assumed statistical model for those properties.

The present invention will be disclosed in greater detail in the remainder of the specification referring to the drawings.

BRIEF DESCRIPTION OF THE DRAWINGS

FIGS. 6A, 6B, 6C, 6D, 6E, and 6F show a series of pictures of a section of the left kidney in which at FIG. 6A an interior sample is inscribed (black polygon) by interactive graphics, and a contour is computed to fit the kidney boundary (dashed), and FIGS. 6B–6F show successive sections with significant variations in the shape details and interior texture of the left kidney.

DETAILED DESCRIPTION OF THE INVENTION

Figure 1:
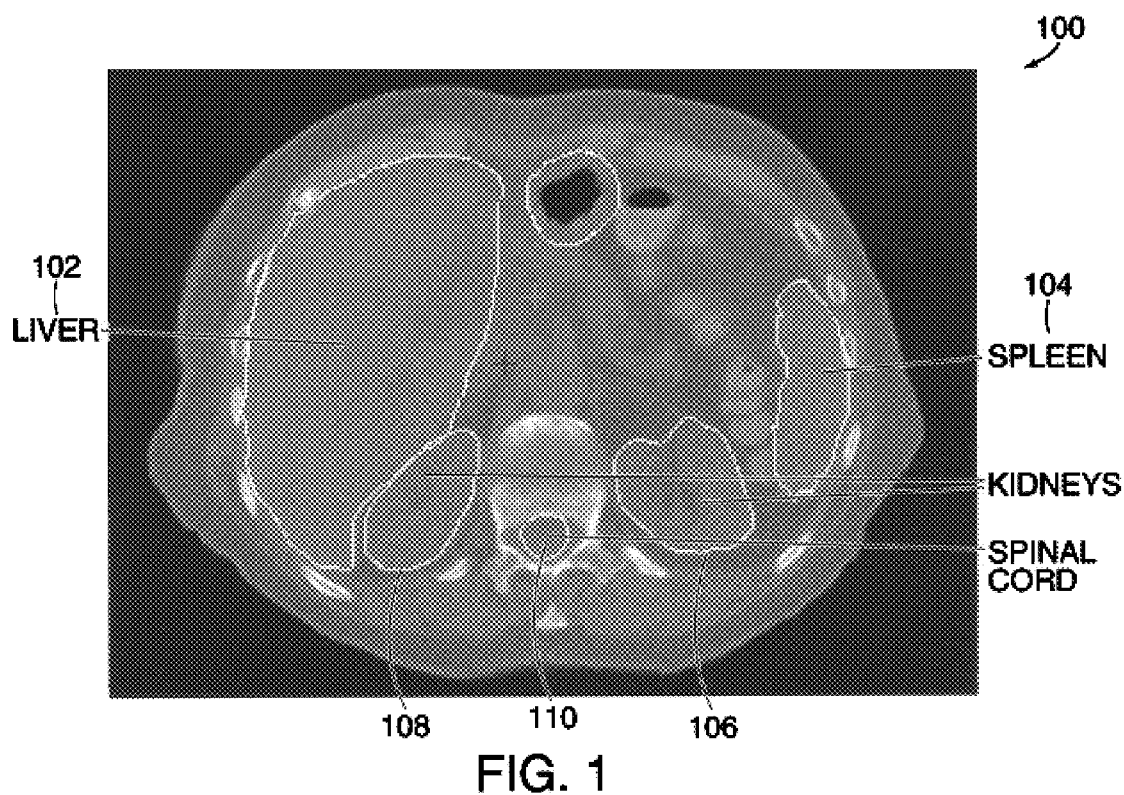
FIG. 1 shows a 2-D CT slice or section image through the abdomen, with certain organ contours labeled.
Figure 2:
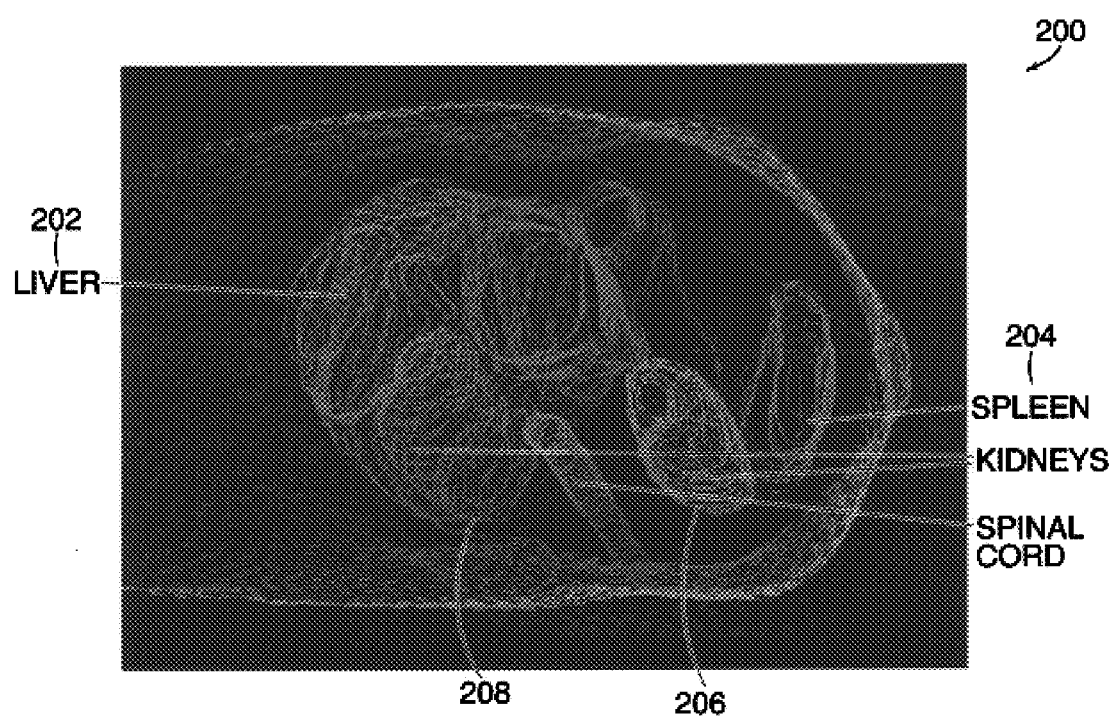
FIG. 2 shows a graphical representation of a 3-D reconstruction of the abdominal anatomy (which incorporates the 2-D CT slice or section image in FIG. 1), with certain organ contours labeled.

The present invention is a system and method for automatically generating accurate 2-D and 3-D contours using maximum a posteriori (MAP) autocontouring/autosegmentation. According to the present invention, the boundary contours of a 3-D tomographic reconstruction of an object may be determined from a contiguous set of 2-D slices or sections. These boundary contours optimally match the local image gray level gradients, the edges of the segmented object with accuracy, and the shape of the prior contour of the object The system and method of the present invention effectively use region, edge, and prior shape information to provide accurate boundary contours in a novel way.

The present invention generates the maximized objective function based on MAP regional growing, MAP boundary detection, and knowledge of the parametric representation of boundary shape. Each of these areas will now be discussed.

Maximum a posteriori (MAP) Regional Growing

Minimum Bayes risk is reported in Van Trees, H. L., *Detection, Estimation, and Modulation Theory, Part I*, Wiley, New York, 1968. According to this reference, minimum Bayes risk is a decision criterion which guarantees, on average, that the results of classification decisions will have the lowest expected loss. That is, if each possible decision outcome is assigned a loss (or cost), Minimum Bays risk decisions will have minimum average loss.

A slightly simpler criterion for classification decision making is minimum Bayes error. Minimum Bayes error is reported in Duda, R. O. and Hart, P. E., *Pattern Classification and Scene Analysis*, Wiley, New York (1973); and Fukunaga, K., *Introduction to Statistical Pattern Recognition*, 2nd Ed., Academic Press, New York (1990). This criterion, which is based on cost=0 for a correct classification decision and cost=1 for an incorrect classification decision, guarantees that the average error of classification will be the lowest possible. As used herein, minimum Bayes error is the criterion for reclassifying an ROI-adjacent, outside pixel as an inside pixel. In addressing minimum Bayes error in greater detail, it will be directed to consideration of all pixels in the inside and outside pixel classes and the computation of a set of gray-level properties or features. A statistically complete description of each feature, in each class, is given by the feature's probability density or histogram. Bayes rules provide the method to compare the features' probability descriptions across classes to make a minimum error decision.

In order to better understand these decision rules for use in the present invention, the following is provided. In this example, X will represent a vector whose component values are the gray-level-derived properties, or features, for a single pixel whose class membership is to be tested. At least some of the features for this single pixel will normally have different values depending on its class, so the probability densities becomes the class conditional probability density $p(X|i)$, which is to mean the probability of observing X given class i. In addition, the relative probability that class i is observed relative to other classes is the a priori probability P(i). Lastly, the probability that class i is the correct class for observation X is the a posteriori probability P(i|X) which is related to the other two probabilities mentioned by Bayes Rule as set forth in Expression (2):

$$P(i|X)=p(X|i)P(i)/\Sigma_k p(X|k)P(k) \quad (2)$$

where,

P(i|X)=the a posteriori probability that class i in the correct class given vector X.

p(X|i)=the conditional probability of observing vector X given class i.

P(i)=the a priori probability that class i is observed.

p(X|k)=the conditional probability of observing vector X given class k.

P(k)=the a priori probability that class k is observed.

$\Sigma_k p(X|k)P(k)$=the sum of the products of the probability of observing vector X given class k and the a priori probability that class k is observed.

P(i|X)=the a posteriori probability that class i is the correct class given vector X.

After reviewing Expression (2) and understanding that it can be applied to two classes, the decision rule for two classes, such as classes i and j, will be to select the class associated with the largest a posteriori probability. This decision rule is embodied by Expression (3):

$$\text{if } P(i|X)>P(j|X), \text{ decide class i, else decide class j} \quad (3)$$

where,

P(i|X)=the a posteriori probability that class i is the correct class given vector X.

P(j|X)=the a posteriori probability that class j is the correct class given vector X.

However, if there are more than two classes, the choice will be the class corresponding to the maximum according to Expression (4):

$$\text{if } i = \underset{j}{\operatorname{argmax}}[P(j|X)], \text{ decide } i \quad (4)$$

where, $$\underset{j}{\operatorname{argmax}}[P(j|X)]$$

=the value of the class label j corresponding to the largest a posteriori probability P(j|X).

The decision rule at Expression (4) represents the maximum a posteriori probability rule. If prior probabilities are unknown, then the conditional probabilities, p(X|i), which are referred to as data likelihoods per Duda, R. O. and Hart, P. E., *Pattern Classification and Scene Analysis*, Wiley, New York (1973), may be combined in the likelihood ratio test of Expression (5):

$$\text{if } \frac{p(X|i)}{p(X|j)} > R, \text{ decide class } i, \text{ else decide class } j \quad (5)$$

where, p(X|i)=the conditional probability of observing vector X given class i.

p(X|j)=the conditional probability of observing vector X given class j.

R=a threshold value greater than zero (0), which can accommodate changes in the estimates of prior probabilities, or give a minimum-error decision on known data (according to Van Trees, H. L., *Detection, Estimation, and Modulation Theory, Part I*, Wiley, New York, 1968).

If, however, the prior probabilities can be estimated, as in the present invention, the MAP probability rule for all classes, as set forth in Expression (3) is the appropriate rule to use.

A review of Expression (2) indicates that it can be written in a more convenient form for use in the method and system of the present invention. From Expression (3), it is understood that p(i|X)∝p(X|i)P(i) because the denominator in Expression (2) is a constant As such, Expression (3) can be written as shown in Expression (6):

$$\text{if } p(X|i)P(i)>p(X|j)P(j), \text{ decide class i, else decide class j} \quad (6)$$

where, p(X|i)=The conditional probability of observing vector X given class i.

P(i)=The a priori probability that class i is observed.

p(X|j)=The conditional probability of observing vector X given class j.

P(j)=The a priori probability that class j is observed.

For reasons of computational convenience, discriminant functions, represented by $g_i()$, of the product p(X|i)P(i) are often used. If the $g_i()$ are monotonically increasing, they may be substituted in Expression (6) without changing the functional nature of the decision rule. Thus, a pixel with vector X is assigned to class i according to Expression (7):

$$\text{if } g_i(X)>g_j(X), i \neq j, \text{ decide class i, else decide class j} \quad (7)$$

where, $g_i(X)$=A function of the a posteriori probability P(i|X).

$g_j(X)$=A function of the a posteriori probability P(j|X).

One such discriminant function is set forth in Expression (8):

$$g_j(X) = \ln p(X|i) + \ln P(i) \quad (8)$$

where, ln p(X|i)=The natural logarithm of the conditional probability of vector X given class i.

ln P(i)=The natural logarithm of the a priori probability of class i.

$g_j(X)$=A function of the a posteriori probability P(j|X).

Parametric forms for the class conditional probability densities p(X|i), p(X|j) can lead to expressions that are more convenient to evaluate. Therefore, with regard to the present invention, there is an assumption that the pixel features are a multivariate, Gaussian distribution that have a class conditional probability density according to Expression (8) (which follows Duda, R. O. and Hart, P. E., *Pattern Classification and Scene Analysis*, Wiley, New York (1973)):

$$p(X|i) = \left[ \frac{1}{(2\pi)^{\frac{d}{2}} |\Sigma_i|^{\frac{1}{2}}} \right] \exp\left[-\left(\frac{1}{2}\right)(X-M_i)^T \sum_i^{-1}(X-M_i)\right] \quad (9)$$

where, d=The number of feature-components in vector X.

$M_i$=The vector of feature means for class i.

$\Sigma_i$=The matrix of covariances for the features in class i.

$\Sigma_i^{-1}$=The inverse covariance matrix for the features in class i.

$|\Sigma_i|$=The determinant of the covariance matrix.

T=Transpose of the given vector.

Now, if Expression (9) is substituted in Expression (8), and the natural logarithm of the density is taken, the result is the discriminant function at Expression (10):

$$g_i(X)=-(1/2)(X-M_i)^T\Sigma_i^{-1}(X-M_i)-(d/2)ln(2\pi)-(1/2)ln\,|\Sigma_i|+ln(P_i) \quad (10)$$

where,

X=Vector X.

$M_i$=The vector of feature means for class i.

$\Sigma_i$=The matrix of covariances for the features in class i $\Sigma_i^{-1}$=The inverse covariance matrix for the features in class i.

$|\Sigma_i|$=The determinant of the covariance matrix.

T=Transpose of the given vector d=The number of feature-components in vector X.

P(i)=The a priori probability that class i is observed.

An understanding of Expression (10) reveals that the $ln(2\pi)$ term can be omitted since it is a constant for all classes.

Keeping in mind Expression (10), the MAP test for two classes i and j according to at least one embodiment of the present invention, is the decision whether to classify a given pixel to the class of pixels belonging to the sample polygon, such as class i, or to the class of pixels outside the sample polygon, such as class j, based on the previously provided in Expression (7), which for convenience is provided here:

$$\text{if } g_i(X) > g_j(X), i \neq j, \text{ decide class i, else decide class j} \quad (7)$$

where, $g_i(X)$=A function of the a posteriori probability P(i|X).

$g_j(X)$=A function of the a posteriori probability P(j|X).

According to Expression (17) the feature vector $X=\{x_1, \ldots x_n\}$ has as its n-components the numeric values of several gray-level-derived measurements on the set of pixels in a neighborhood about each pixel. At least the use of the first order gray-level properties are reported in Pratt, W. K., *Digital Image Processing*, 2nd Ed., Wiley, New York (1991). The numeric values can include the mean, standard deviation, skewness, kurtosis, energy, entropy, and the range, but also other texture measures. However, it is understood that there can be more gray-level-derived properties for which numeric values may be generated.

The neighborhood that has been referred to preferably is a 3×3-pixel set, or the 8 pixels adjacent to the given pixel, minus any pixels not inside the ROI. From the values of the X-components, the mean feature vectors $M_i$ and the covariance matrices $\Sigma_i$ can be computed and inserted into the Expression (10) for use in the decision rule at Expression (7).

Figure 3:
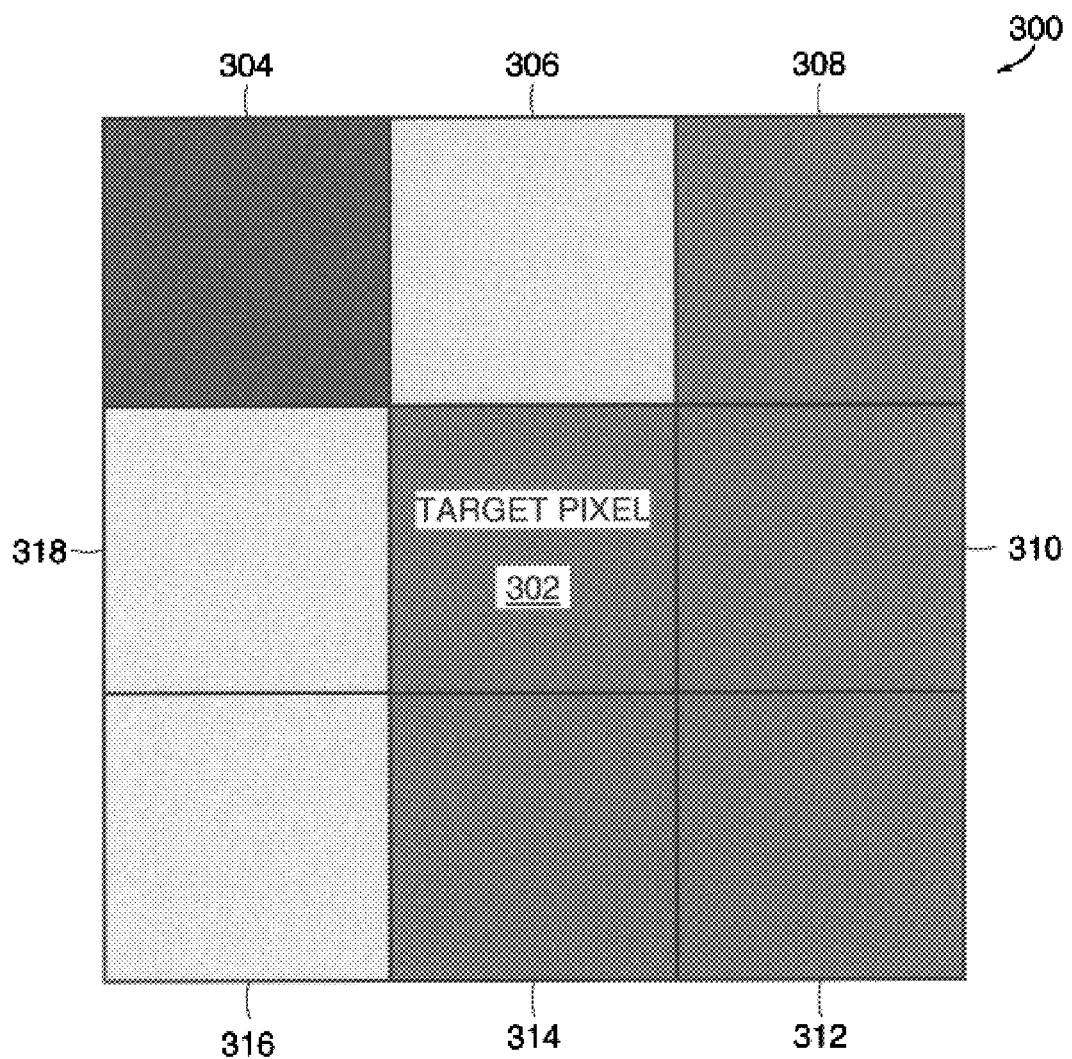
FIG. 3 is a graphical representation of a target pixel and the 3×3 set of pixels that influence the properties of the target pixel.

A representative 3×3 pixel set is shown graphically in FIG. 3, generally at 300. In FIG. 3, the pixel of interest is center pixel 302. The pixels that influence the numeric values of center pixel 302 are the 8 pixels adjacent to it. These are pixels 304, 306, 308, 310, 312, 314, 316, and 318. These 8 pixels and the center pixel form the 3×3 pixel set except for pixels at, or adjacent to, the boundary of the polygon which fall outside the ROI.

Autocontouring/autosegmentation according to the present invention imposes three constraints on the probabilistic growth of the ROI to match to an image object boundary. The first is that the initial ROI polygon be entirely within the object being contoured. If the initial ROI polygon spans the boundaries between different anatomic structures, the present invention will not expand the boundary properly.

The second is that the ROI grows only be accreting former outside pixels. As such, no inside pixels are allowed to revert to outside at any point in the growth process. The third constraint is that any outside pixels that become completely surrounded by inside pixels are converted to be inside pixels. Thus, the resulting ROI perimeter will define a simply connected object. Given the foregoing, the application of the decision rules and the constraints in the context of the present invention will now be described.

Maximum a posteriori (AP) Boundary Detection:
MAP Objective Function

On average, the shapes of objects appearing in two or more serial-section images satisfy three properties: (1) the object boundaries coincide with local maxima in the magnitude of the gray level gradient, (2) the boundary-enclosed regions have nearly homogenous textures, and (3) profiles of objects in a given section will be similar to those in the adjacent sections. Homogeneous textures are gray-level properties that have constant means and variances across the whole region. The degree to which any trial contour coincides with local gradients and segmented region-edges, and agrees with shapes of prior contours, depends on the details of its shape.

According to the present invention, computed contours are represented by continuous functions of shape parameters. Thus, the (x,y) coordinates of the points on the contour are themselves functions of the arc-length distance along the curve, t, along with the set (or vector) of parameters p, (x(p,t),y(p,t)). If the total length of the contour is T, then $0 \leq t < T$. The values of the parameters are given by equations for the Fourier elliptic representation which are described in detail below in the section entitled "Parametric Representation of Boundary Shape."

The contour parameters also serve as independent variables for the objective function that (1) measures the region-edge and gradient-edge overlap, and (2) the similarity of the current contour with prior contours. Properly defined, this objective function assumes a maximum value for the set of parameters p that correspond to the contour which most satisfies the three criteria stated at the beginning of this section. The objective function used in the system and method of the present invention is a function of the conditional probability reported in Chakraborty, A., Staib, L. H., Duncan, J. S., *Deformable boundary finding in medical images by integrating gradient and region information*, IEEE Transactions on Medical Imaging, 15:859–870 (1996). This objective function is in the form of Expression (11):

$$P(p|I_r, I_g) \quad (11)$$

where,

P=a set or vector of real-value parameters.

$I_r$=the region-classified image.

$I_g$=the gray-level gradient image.

The probability depicted by Expression (11) is the probability of obtaining the contour with parameter vector p given the region-classified image $I_r$, and the image of the scalar magnitude of the gray level gradient $I_g$. The components of parameter vector p are treated as random variables, and parameter vector p is assumed to have a multivariate, Gaussian distribution probability density.

It is reported in Chakraborty, A., Staib, L. H., and Duncan, J. S., *Deformable boundary finding in medical images by integrating gradient and region information, IEEE Trans-* actions on Medical Imaging, 15-859-870 (1996) to use Bayes rule and the relationship between joint and conditional probabilities to derive the expression for $P(p|I_r, I_g)$ in terms of measurable image quantities. The expression that is derived is at Expressions (12A, 12B, and 12C):

$$P(p \mid I_r, I_g) = \frac{P(p, I_r, I_g)}{P(I_g, I_r)} \quad (12A)$$

$$= \frac{P(I_r \mid I_g, p) P(p, I_g)}{P(I_g, I_r)} \quad (12B)$$

$$= \frac{P(I_r \mid I_g, p) P(p, I_g) P(p)}{P(I_g, I_r)} \quad (12C)$$

where, $P(p, I_r, I_g)$=The joint probability of contour vector p, $I_r$, and $I_g$.
$P(I_r|I_g,p)$=The conditional probability of $I_r$ given $I_g$ and p.
$P(p, I_g)$=The joint probability of contour vector p and $I_g$.
$P(I_g, I_r)$=The joint probability of contour vector $I_g$ and $I_r$.
$P(p|I_g)$=The conditional probability of p given $I_g$.
$P(p)$=The a priori probability of the contour p.
$I_r$=The region-classified image produced by the MAP region growing method described above.
$I_g$=The gray-level gradient image.

In Expression (12A)–(12C), the denominator is constant, and furthermore, the natural logarithm is a monotonically increasing function. Therefore, an equivalent expression for the boundary parameter values, which will be expressed as p* and maximize $P(p|I_r, I_g)$, can be derived from Expression (13):

$$p^* = \underset{p}{\mathrm{argmax}} [\ln P(I_r \mid I_g, p) + \ln P(p \mid I_g) + \ln P(p)] \quad (13)$$

where, p*=boundary parameter values.

$$\underset{p}{\mathrm{argmax}}[\ ]$$

=The argument corresponding to the largest term within the brackets.

$P(I_r|I_g,p)$=The conditional probability of $I_r$ given $I_g$ and p.
$\ln P(p|I_g)$=The natural logarithm of the conditional probability of p given $I_g$.
$\ln P(p)$=The natural logarithm of the a priori probability of values for p.

Referring to Expression (13), the first term is the natural logarithm of the probability of a region image $I_r$ given gradient image $I_g$ and contour parameters p. The second term is the natural logarithm of the probability of obtaining a contour parameters p given the gradient image $I_g$. The third term is the natural logarithm of the probability of a given contour parameters p. Obtaining actual probability measures is difficult because sufficient information about the space of possible outcomes is not available. Chakraborty, A., Staib, L. H., and Duncan, J. S., *Deformable boundary finding in medical images by integrating gradient and region information, IEEE Transactions on Medical Imaging,* 15:859–870 (1996) addressed this issue by rewriting Expression (14) to make explicit the dependencies of the terms on the various image properties, in a way related to, but not dependent on any probabilities. This resulted in Expression (14):

$$\underset{p}{\mathrm{argmax}} M(p, I_g, I_r) = \quad (14)$$

$$\underset{p}{\mathrm{argmax}}[M_{prior}(p) + M_{gradient}(I_g, p) + M_{region}(I_r, p)]$$

where, $$\underset{p}{\mathrm{argmax}} M(p, I_g, I_r)$$

=the contour parameter vector p that corresponds to the largest value of the objective function M of p, $I_g$, and $I_r$.

$$\underset{p}{\mathrm{argmax}} M[\ ]$$

=the value of the contour parameters p corresponding to the largest value of the term in the brackets.

$M_{prior}(p)$=the function of the similarity of contour parameters p and the parameters of the corresponding contour of a neighboring section.

$M_{gradient}(I_g, p)$=the function of the similarity of the gradient maxima and the contour specified by parameters p.

$M_{region}(I_r, p)$=the function of the similarity of the classified region edge and the contour specified by parameters p.

According to Expression (14), the first (prior) term biases the boundary toward a particular distribution of shapes generated from prior experience. The second (gradient) term contributes the most when the parametric boundary p, defined as the discrete boundary x(p,t),y(p,t), most closely matches the coherent edge features in $I_g$. The third (region) term is maximized when the parametric boundary p most closely matches the edges of the segmented region. The determination of these individual terms will be discussed in detail below.

a. Region Edge Contributions to the MAP Function: $M_{region}(p,I_r)$

The value of the $M_{region}(p,I_r)$ term in Expression (14) depends on the match of the parametric boundary with the edge of the region. Chakraborty, A., Staib, L. H., Duncan, J. S., *Deformable boundary finding in medical images by integrating gradient and region information, IEEE Transactions on Medical Imaging,* 15:859–870 (1996) describes a method to maximize the exactness of the fit. This method rewards the boundary that contains as much of the inside region as possible, and penalizes the boundary that includes any of the outside pixels. The desired result is obtained by integrating over the area of a region template $A_p$ according to Expression (15):

$$M_{region}(I_r, p) = \iint_{A_p} I_r(x,y) dA_p \quad (15)$$

where, $I_r$=the region-classified image.
p=a set of real-value parameters.
$A_p$=the area of the region template.

In evaluating Expression (15), it is understood that the template pixels inside the region are set equal to +1 and outside pixels are −1. Thus, $M_{region}(p,I_r)$is maximized when p conforms to the edge of the region of +1's. Because the area integral must be evaluated many times in the maximization of $M(p,I_g,I_r)$, Chakraborty, A., Staib, L. H., Duncan, J. S., *Deformable boundary finding in medical images by integrating gradient and region information, IEEE Transactions on Medical Imaging,* 15:859–870 (1996) describes an alternative integration method based on Green's Theorem which can be evaluated more rapidly. This alternative method will now be described.

The alternative integration method based on Green's Theorem, results in the decomposition of the integral area into two line integrals which can be evaluated more rapidly. Green's Theorem, as reported in Kaplan, W., *Advanced Calculus, Addison-Wesley,* Reading, Mass., 1952, specifies that the area integral according to Expression (16) can be written as the sum of two line integrals, as shown in Expression (16):

$$\int\int_{A_p} I_r(x,y) dA = \frac{1}{2} \int_{C_p} \left[ N_r(x,y)\frac{\partial x}{\partial t} + M_r(x,y)\frac{\partial y}{\partial t} \right] dt \quad (16)$$

where,
$I_r$=the region-classified image.
(x,y)=the x,y coordinates of any point in $I_r$
$A_p$=the area of the region template.
$N_r$, $M_r$=the auxiliary functions defined in Expressions (17) and (18) below.
t=the arc-length distance of a point (x,y) from an origin point.

In view of Expression (16), the two terms to be integrated, $M_r$ and $N_r$, may be written as Expressions (17) and (18):

$$M_r(x,y) = \int_0^x I_r(z,y) dz \quad (17)$$

$$N_r(x,y) = -\int_0^y I_r(x,z) dz \quad (18)$$

where,
$I_r$=The region-classified image.
(x,y)=The x and y coordinates of a point.
z=Dummy variable of integration.

The image $I_r$ contains a template of the segmented region with pixel values of one (1) for pixels inside the region, and −1 for pixels outside the region. Evaluating Expression (16) from the discrete image data is traversing the parametric boundary curve $C_p$ (in the plane of $A_p$) by summing values from 2-D arrays containing the sums $M_r$, $N_r$ as set forth in Expression (19):

$$M_{region}(I_r, p) \propto \frac{1}{2} \sum_{k=1}^{K} \left[ N_r(x(p,t)_k, y(p,t)_k) \Delta \frac{x(p,t)_k}{\Delta t} + M_r(x(p,t)_k, y(p,t)_k \Delta \frac{x(p,t)_k}{\Delta t} \right] \quad (19)$$

where,
$M_{region}$ ($I_r$, p)=the function of the similarity of the region-classified edge and the contour specified by parameters p.
K=the length of the contour in pixels.
$N_r$, $M_r$=the auxiliary functions defined in Expressions (17) and (18) above.
x(p,t)=the x coordinate for specific values of parameters p and arc-length distance t.
y(p,t)=the y coordinate for specific values of parameters p and arc-length distance t.

Δx=the finite difference computed from actual x values at pixel locations.
Δy=the finite difference computed from actual y values at pixel locations.
Δt=the finite difference computed from actual t values at pixel locations.

This sum set forth in Expression (19) is over all the K-points in contour $C_p$, and the Δ-differentials are evaluated by taking discrete differences. Discrete forms of $M_r$, $N_r$ are given by Expressions (20) and (21), respectively:

$$M_r(x,y) = \sum_{z=0}^{x} I_r(z,y) \quad (20)$$

$$N_r(x,y) = -\sum_{z=0}^{y} I_r(x,z) \quad (21)$$

where,
$N_r$, $M_r$=the auxiliary functions defined above.
(x,y)=the (x,y) coordinates of a point.
$I_r$=the region-classified image.
z=the index of sums over x or y coordinates.

Noting the foregoing, the first term of Expression (14) has been described.

b. Gradient Edge Contributions to the MAP Function

The second term in Expression (14), $M_{gradient}(p,I_g)$, depends on the coincidences of the parameterized boundary with edges in the image appearing as coherent features in the scalar gradient of the original image gray levels. The gradient term is a contour integral whose domain is the parametric contour $C_p$ realized by the discrete boundary [x(p,t), y(p,t)]. In reviewing Staib, L. H. and Duncan, J. S., *Boundary finding with parametrically deformable models, IEEE Transactions on Pattern Analysis and Machine Intelligence,* 14:1061–1075 (1992), it is found that it is assumed that $I_g$ contains a zero-mean noise process and independent boundary pixels making it possible to evaluate $M_{gradient}(p,I_g)$ as the line integral according to Expression (22):

$$M_{gradient}(p, I_g) = \frac{k_1}{\sigma^2} \int_{C_p} I_g[x(p,t), y(p,t)] dt \quad (22)$$

where,
$I_g$=The gray-level gradient image.
$k_1$=a constant.
p=a set of real-value parameters.
x(p,t)=the x coordinate for values of parameters p and arc-length distance t.
y(p,t)=the y coordinate for values of parameters p and arc-length distance t.
$\sigma^2$=the noise variance.

The likelihood of p representing the true boundary is proportional to the sum of the gradient values at all the points x(p,t),y(p,t) which will be used to evaluate the term $M_{gradient}(I_g,p)$ over the K discrete contour pixels according the Expression (23):

$$M_{gradient}(I_g, p) = \sum_{k=1}^{K} I_k(x(p, t)_k, y(p, t)_k) \quad (23)$$

where, $I_g$=The gray-level gradient image.

K=the length of the contour in pixels.

p=a set of real-value parameters.

x(p,t)=the x coordinate for values of parameters p and arc-length distance t.

y(p,t)=the y coordinate for values of parameters p and arc-length distance t.

Given the foregoing, the second term of Expression (14) has been described.

c. Prior Contour Shape Contributions to the MAP Function

The third term of Expression (14) is $M_{prior}(p)$. With regard to this term, it is assumed that the components of $p=\{p_1, p_2, \ldots, p_{4n+2}\}$ form a multivariate, Gaussian distribution. It is also assumed, however, that each component $p_i$ of the distribution set is statistically independent. The component probability densities $P(p_i)$ are set according to Expression (24):

$$P(p_i) = \frac{1}{\sigma_i \sqrt{2\pi}} \exp\left(-\frac{(p_i - m_i)^2}{2\sigma_i^2}\right) \quad (24)$$

where, $p_i$=the i-th component of the contour parametric vector p.

$\sigma_i$=the standard deviation for the component $p_i$ of the contour vector p.

$m_i$=the mean value for the component $p_i$ of the contour vector p.

Given Expression (24), the total probability for the multivariate, Gaussian distribution set is according to Expression (25):

$$M_{prior}(p) = \prod_{i=1}^{n} P_r(p_i) \quad (25)$$

The prior contour shape contribution to $M(p, I_g, I_r)$ is found by combining Expressions (24) and (25) to get the products that is set forth in Expression (26):

$$M_{prior}(p) = \prod_{i=1}^{n} P_r(p_i) = \prod_{i=1}^{n} \frac{1}{\sigma_i \sqrt{2\pi}} \exp\left(-\frac{(p_i - m_i)^2}{2\delta_i^2}\right) \quad (26)$$

where, $p_i$=the i-th component of the contour vector p.

$\sigma_i$=the standard deviation for the component $p_i$ of the contour vector p.

$m_i$=the mean value for the component $p_i$ of the contour vector p.

Parametric Representation of Boundary Shape

The functional form of the boundary parameterization is the Fourier elliptical representation. This is reported in Giardina, C. R. and Kuhl, F. P., *Accuracy of curve approximation by harmonically related vectors with elliptical loci, Computer Graphics and Image Processing*, 6:277–285 (1977); and Kuhl, F. P. and Giardina, C. R., *Elliptic Fourier features of a closed contour, Computer Graphics and Image Processing*, 18:236–258 (1982). According to these references, an object boundary contour is considered to be a closed, continuous curve V(p,t), where t is the arc-length and p is the parameter vector. The curve has a total length T, such that $0 \leq t < T$. The curve function V depends on the discrete pixels located at (x(p,t),y(p,t)) as set forth in the Expression (27):

$$V(p, t) = \begin{bmatrix} x(p, t) \\ y(p, t) \end{bmatrix} \quad (27)$$

wherein x(p,t) the x coordinate for values of parameter p and arc-length distance t.

y(p,t)=the y coordinate for values of parameter p and arc-length distance t.

p=a set of real-value parameters.

t=the arc-length distance of a point (x(p,t),y(p,t)) from an origin point.

The functions (x,(p,t),y(p,t)) are periodic in arc-length distance, t, with the period of the total curve length, T. These are approximated by the finite Fourier series shown at Expressions (28) and (29):

$$x(p, t) = a_o + \sum_{n=1}^{N} a_n \cos \frac{2n\pi t}{T} + b_n \sin \frac{2n\pi t}{T} \quad (28)$$

$$y(p, t) = c_o + \sum_{n=1}^{N} c_n \cos \frac{2n\pi t}{T} + d_n \sin \frac{2n\pi t}{T} \quad (29)$$

In Expressions (29) and (30), the contour vector p is the set of Fourier coefficients $\{a_0, c_0, a_1, b_1, c_1, d_1, \ldots, a_n, b_n, c_n, d_n\}$, and N is the total number of Fourier harmonics. Maximization of the objective function, $M(p, I_g, I_r)$, is carried out over the vector $\{p_1, p_2, \ldots p_{4N+2}\}$, and the resulting contour is computed directly using Expressions (28) and (29). The parameterization is global in that each parameter $p_i$ makes a contribution to (x(p,t),y(p,t)) at every value of t.

As an example, to compute the contour parameters $\{a_0, c_0, a_1, b_1, c_1, d_1, \ldots, a_n, b_n, c_n, d_n\}$ from the coordinates (x(p,t), y(p,t)), Expressions (30)–(35) may be used $$a_n = \frac{T}{2n^2\pi^2} \sum_{k=l}^{K} \frac{\Delta x_k}{\Delta t_k} \left[\cos \frac{2n\pi t_k}{T} - \cos \frac{2n\pi t_{k-1}}{T}\right] \quad (30)$$

$$b_n = \frac{T}{2n^2\pi^2} \sum_{k=l}^{K} \frac{\Delta x_k}{\Delta t_k} \left[\sin \frac{2n\pi t_k}{T} - \sin \frac{2n\pi t_{k-1}}{T}\right] \quad (31)$$

$$c_n = \frac{T}{2n^2\pi^2} \sum_{k=l}^{K} \frac{\Delta y_k}{\Delta t_k} \left[\cos \frac{2n\pi t_k}{T} - \cos \frac{2n\pi t_{k-1}}{T}\right] \quad (32)$$

$$d_n = \frac{T}{2n^2\pi^2} \sum_{k=l}^{K} \frac{\Delta y_k}{\Delta t_k} \left[\sin \frac{2n\pi t_k}{T} - \sin \frac{2n\pi t_{k-1}}{T}\right] \quad (33)$$

where, $\Delta x$=the finite difference computed from actual x(k) values at pixel locations.

$\Delta y$=the finite difference computed from actual y(k) values at pixel locations.

$\Delta t$=the finite difference computed from actual t values at pixel locations.

K=the length of the contour in pixels.

T=the total contour length.

t=the arc-length distance of a point x(k),y(k) from an origin point.

The remaining terms, constant $a_0$, $c_0$, are computed as follows according to Expressions (34) and (35):

$$a_0 = \frac{1}{T}\sum_{k=1}^{K}\frac{\Delta x_k}{2\Delta t_k}(t_k^2 - t_{k-1}^2) + \xi_k(t_k - t_{k-1}), \xi_k = \sum_{j=1}^{k-1}\Delta x_j - \frac{\Delta x_k}{\Delta t_k}\sum_{j=1}^{k-1}\Delta t_j \quad (34)$$

$$c_0 = \frac{1}{T}\sum_{k=1}^{K}\frac{\Delta y_k}{2\Delta t_k}(t_k^2 - t_{k-1}^2) + \delta_k(t_k - t_{k-1}), \delta_k = \sum_{j=1}^{k-1}\Delta y_j - \frac{\Delta y_k}{\Delta t_k}\sum_{j=1}^{k-1}\Delta t_j \quad (35)$$

where,

Δx=the finite difference computed from actual x values at pixel locations.

Δy=the finite difference computed from actual y values at pixel locations.

Δt=the finite difference computed from actual t values at pixel locations.

K=the length of the contour in pixels.

T=the total contour length.

t=the arc-length distance of a point x(k),y(k) from an origin point.

$\xi_1 = \delta_1 = 0$.

The set of Expressions (30)–(35) have been reported in Kuhl, F. P. and Giardina, C. R., *Elliptic Fourier features of a closed contour*, Computed Graphics and Image Processing, 18:236–258 (1982).

Given the Expressions (28) and (29), there is the need to know the number of Fourier harmonics, N, that are required for an acceptable approximation of a parametric contour for a given boundary. In this context, as the total length of the contour, T, increases, the number of Fourier harmonics possible increases with the support available for representation. However, there is an optimal number of Fourier harmonics for a given T. If the number of Fourier harmonics is increased from some small number, the corresponding contours display increasingly good agreement with the object boundary until the optional number is reached. However, there is a value of N beyond which the contours are increasingly degraded.

The improved approximation occurs as N increases from a small number because the shape of the boundary is better captured by adding more information to the contour representation. Continuing to increase N past the optimum, however, inevitably produces noisy contours because the Fourier coefficients are underdetermined with respect to the number of discrete pixels in the contour. This degradation is especially evident when the ratio of the number of contour-pixels K to the number of p-parameters (=4N+2) falls below 2.0.

The behavior just described is consistent with the fact that small objects rarely have sharp corners needing high frequency representations by a large number of harmonics. Large objects such as the liver, for example, frequently have sharp turns in their boundaries but are well-represented by the large number of harmonics available because of the correspondingly larger supports (contour lengths). Thus, adapting the number of harmonics to the size of the object works because objects in CT and MRI are inherently (shape) band-limited, and, therefore, may be represented accurately by finite-length Fourier series.

The relationship between the number of harmonics producing the best boundary-contour match and the contour length may be obtained, for example, by examining the contours produced for a series of abdominal organs with boundary lengths spanning an order of magnitude (see FIGS. 4A–4F). For each object, contours may be computed with increasing numbers of harmonics until the good matches are succeeded by noisy contours (see FIGS. 5A–5D). Plotting the number of harmonics needed to produce the best match versus the contour length results * in a log-linear relationship according to Expression (36):

$$N * \begin{cases} 2 & \text{if } \log_{10}K \leq 21 \\ \text{int}(12.0 * \log_{10}K - 22.4) & \text{if } \log_{10}K > 21 \end{cases} \quad (36)$$

where,

K=the length of the contour in pixels.

int=the operation of taking the nearest integer of the argument in parentheses.

N*=the number of Fourier harmonics.

Expression (36) permits the system and method of the present invention to adapt to objects of varying size.

The set of parameters p in Expression (1) serve as independent variables of the objective function $M(p, I_r, I_g)$, described above. The objective function assumes greater or lesser values (and significance) depending on the correlation of the computed, parametric contour and the actual object boundary of the image. The objective function is based on the sum of functions of the a posteriori probabilities of the computed, parametric contour given:

(1) the quality of the match of the computed boundary with the perimeter of the interior region of the actual object;

(2) the coincidence of the computed boundary with local gray level gradient maxima; and (3) the similarity of the shapes of the estimated boundary with previously-determined, section boundaries for the computed contour.

The estimation and growing of the computed contour is based on the Baysian formulation of the objective function which insures that a maximum a posteriori (MAP) result will be associated with the minimum average error in computed, contour determinations.

Now having described the components that result in the maximization of the computed contour, the implementation of the system and method of the present invention will be described.

Implementation of the Preferred Embodiment

The system and method of the present invention are used to generate computed contours that may be used for 2-D contouring and 3-D reconstructions, for example, of an anatomical areas of interest. The system and method of the present invention use data from the previously-contoured sections to generate contours for other sections, automatically, and without any user input. Generation of an initial contour does require interactive input, and that part of the system and method of the present invention will be described following the description of the automated contouring method.

For the purpose of describing the implementation of the present invention, some of the quantities that are generated during a current section's analysis take a new value during each step of the iterative region growing, and this will be indicated by the double superscript$^{(k,l)}$, where, k is the section number and l is the iteration step. A single superscript will indicate that the quantity is the final result of the contour determination for that section.

The following is a description of an embodiment of the system and method of the present invention.

The first action that takes place is that the present invention locates the pixels in the current section, $I_r^{(k,l=0)}$ coincident with $I_r^{(k-1)}$ by classifying the current k− section pixels with the (k−1) texture classifier. The largest connected set of k pixels similar to the (k−1) contour interior-pixels is the starting point for iterative region growing.

The present invention next makes a new texture classifier using the pixels inside and outside of $I_r^{(k,l=0)}$. At that juncture, for each class i, the mean vectors $m_i^{(k)}$ and inverse covariance matrices $[\Sigma_i^{-1}]^{(k)}$ are computed. Only one set of mean vectors and covariances are computed for each class i for the current section k.

The present invention then computes the image of the gray-level gradients for the current section $I_g^{(k)}$. Once this is done, the present invention increments l by one, l=l+1.

The present invention expands $I_r^{(k,l-1)}$ by one pixel layer to form $I_r^{(k,l)}$, and re-enumerates all the region perimeter pixels.

The present invention then forms from the $I_r^{(k,l)}$ perimeter pixels, a set of contour parameters, $p^{(k,*)}$, and probability densities $P(p^{(k,*)})$, where * indicates that these form the initial value set before maximization of the objective function, and where the number of parameters (components of p) is varied with respect to the length of the contour to obtain the minimum-error match of contour to boundary.

The present invention then maximizes the objective function in terms of the p parameters. The l-th cycle function is $M^{(k,l)}$ ($p^{(k,l)}$, $I_g^{(k)}$,$I_r^{(k,l)}$) with the superscripts indicating that parameters $p^{(k,l)}$ and region-increment $I_r^{(k,l)}$ are specific to present iteration step.

The present invention then tests the growth of the region to determine if it is at the maximum based on the decision rules for growth. This test is according to the following procedures:

If l>2, and if l=the maximum allowed number of iterations or if $M^{(k,l)}<M^{(k,l-2)}$, then the present invention will find the largest $M^{(k,l)}$ according to the Expression (37) using the values at the current interation step:

$$M^{(k)}(p^{(k)}, I_g^{(k)}, I_r^{(k)}) = \max_l [M^{(k,l)}(p^{(k,l)}, I_g^{(k)}, I_r^{(k,l)})] \quad (37)$$

In Expression (37), the single superscript indicates that these are the optimal results to be saved and used for determining the (k+1) section. If, however, the predicate questions indicated immediately above are not satisfied, then the present invention will increment l by 1 and repeat the steps to this point in the growth of the region, beginning with the step in which $I_r^{(k,l)}$ is expanded by one pixel layer to form $I_r^{(k,l)}$.

Once the largest $M^{(k,l)}$ is determined using Expression (37), the current k-th section results are saved. The information saved is (a) the template of interior of contour, $I_r^{(k)}$;
(b) the feature mean vector for each class i, $m_i^{(k)}$, i={inside, outside};
(c) the feature inverse covariance matrix for each class i, $[\Sigma_i^{-1}]^{(k)}$
(d) the determinant of covariance matrix for each class i, $|\Sigma_i|^{(k)}$
(e) the shape parameters $p^{(k)}=\{\ldots p_i \ldots\}^{(k)}$ and probability densities $P(p^{(k)})$.

Now that this is completed, k is incremented by 1 for a new section and the process is repeated for this new section to be contoured.

Having now described the method by which the ROI is grown to match the contour of a desired anatomical or other image, it is necessary to describe the method by which the initial ROI is generated.

The initial contour is generated on the first section, k=0, by the user sampling the interior of the object to contoured. The ROI (or polygonal sample) that is generated is the starting point for the region growing that has been described which uses a text classifier based on pixels inside and outside the initial ROI. The texture classifier has feature mean vectors and covariance matrices according to the following:

(a) the feature mean vector for each class i, $m_i^{(0)}$, i={INSIDE, OUTSIDE};
(b) the feature inverse covariance matrix for each class i, $[\Sigma_i^{-1}]^{(0)}$;
(c) the determinant of the covariance matrix for each class i, $[\Sigma_i]^{(0)}$.

Each pixel outside of, and adjacent to, the ROI is tested, and if it is more like the inside pixels, its label is changed from OUTSIDE to INSIDE. The present invention then re-enumerates all the perimeter pixels, and repeats the testing of all outside, ROI-adjacent pixels. This process is repeated until no further adjacent pixels pass the test. The last ROI is taken to be $I_r^{(0)}$. From the $I_r^{(0)}$ perimeter pixels, a set of contour parameters and probability densities, $p^{(*)}$, $P(p^{(*)})$ are formed, where * indicates that these are initial values set before maximization of the objective function, and where the number of parameters (components of p) is varied with respect to the length of the contour to obtain the minimum-error match of the contour boundary. The image of the gray level gradient values is then computed, $I_g(0)$. The set of contour parameters p(0) corresponding to the maximum of the objective function, $M^{(0)}(p^{(*)}, I_g^{(0)},I_r^{(0)})$, is according to Expression (38), $$p(0) = \underset{p^{(*)}}{\operatorname{argmax}}[M^{(0)}(p^{(*)}, I_g^{(0)}, I_r^{(0)})] \quad (38)$$

Now that the initial ROI is formed, the following parameters are saved so that the ROI may be grown using the region growing method starting with the next section, k=1:

(a) the template of the interior of contour, $I_r^{(k-1)}=I_r^{(0)}$;
(b) the feature mean vector for each class i, $m_i^{(k-1)}$, $m_i^{(0)}$, i={INSIDE, OUTSIDE};
(c) the feature inverse covariance matrix for each class i, $[\Sigma_i^{-1}]^{(k-1)}=[\Sigma_i^{-1}]^{(0)}$;
(d) the determinant of the covariance matrix for each class i, $|\Sigma_i|^{(k-1)}=|\Sigma_i|^{(0)}$;
(e) the shape parameters, $p^{(k-1)}=\{\ldots p_i \ldots\}^{(k-1)}=\{\ldots p_i \ldots\}^{(0)}$ and the probability densities $P(p^{(k-1)})=P(p^{(0)})$.

The system and method of the present invention have been described in detail above, now representative results on the operation of this system method will be described.

Representative Results a. Computed Contours as a Function of the Number of Harmonics FIGS. 4A–4F show a series of regions that have been grown using different values of Fourier harmonics, N. More specifically, these figures consist of a series of synthetic pictures in which the boundary (black) to be contoured is defined a priori by a fixed set of parameters p and the computed contour (white) corresponds to the best or maximum $M(p,I_g,I_r)$ objective function for the different numbers of Fourier harmonics, N. A comparison of the number of Fourier harmonics, N, and the RMS error values for FIGS. 4A–4F is shown in Table 1:

TABLE 1

| Figure | N | RMS error |
|---|---|---|
| 4A | 2 | 6.8 |
| 4B | 4 | 5.1 |
| 4C | 8 | 1.6 |
| 4D | 16 | 0.69 |
| 4E | 32 | 0.61 |
| 4F | 64 | 0.69 |

Figure 4A:
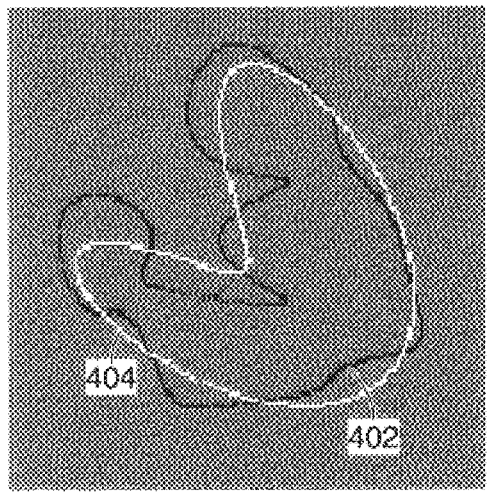
FIGS. 4A, 4B, 4C, 4D, 4E, and 4F show a series of synthetic pictures in which the boundary (black) to be contoured is defined a priori by a fixed set of parameters p, and the computed contour (white) corresponds to the best, or maximum $M(p,I_g,I_r)$ objection function, for varying numbers of Fourier harmonics, N.
Figure 4B:
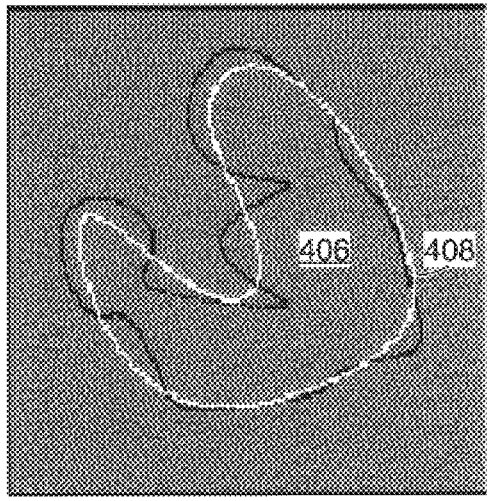
Figure 4C:
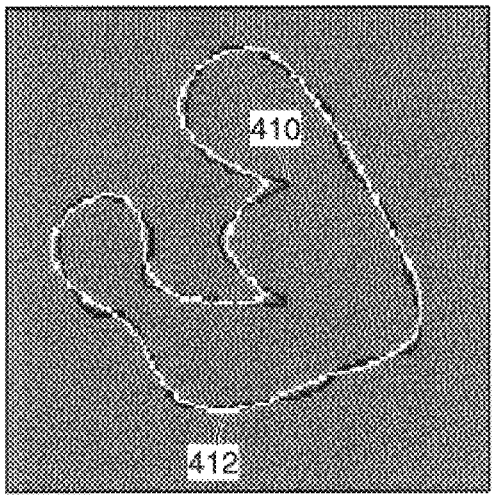
Figure 4D:
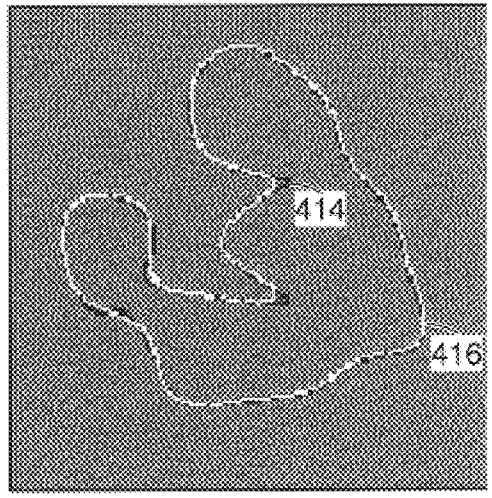
Figure 4E:
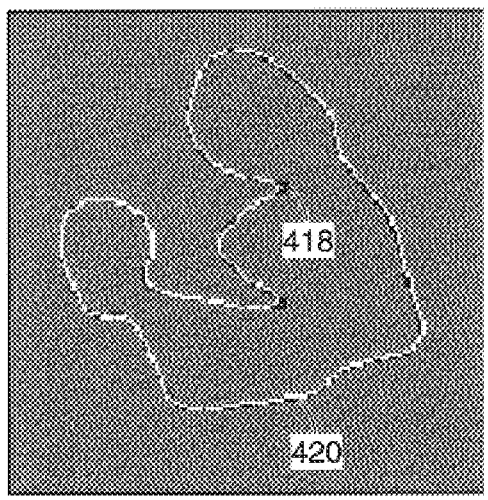
Figure 4F:
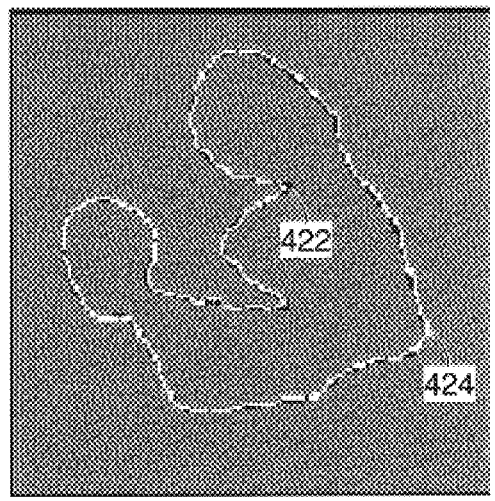

As shown in Table 1, the number of Fourier harmonics $N=2^n$, n=1 to 6. FIG. 4A shows boundary 402 and computed contour 404; FIG. 4B shows boundary 406 and computed contour 408; FIG. 4C shows boundary 410 and computed contour 412; FIG. 4D shows boundary 414 and computed contour 416; FIG. 4E shows boundary 418 and computed contour 420; and FIG. 4F shows boundary 422 and computed contour 424. A review of the match between the boundary and computed contour in the FIGS. 4A to 4F, respectively, reveals that there is improved matching as the number of Fourier harmonics is increased, with the best match (minimum error) occurring at 32 Fourier harmonics.

In the set of matches defined by FIGS. 4A to 4F, it is readily seen that the match between boundary 402 and computed contour 404 in FIG. 414 and boundary 406 and computed contour 408 in FIG. 4B is not particularly good because much of the detail of the boundaries are not found in the contours. It is to be noted that FIGS. 4A and 4B correspond to Fourier harmonic values of 2 and 4, respectively. It also is to be noted that the RMS (root mean square) error values are high for these harmonics. These high values are 6.8 for FIG. 4A and 5.1 for FIG. 4B.

FIG. 4C, which used 8 Fourier harmonics, has a significantly improved match between boundary 410 and computed contour 412. Table 1 also shows that the RMS error value has significantly decreased to 1.6 compared to the RMS error values of 6.8 and 5.1 for Fourier harmonics values of 2 and 4, respectively. Even with the improved matching in FIG. 4C, some of the detail of the boundary is missing in the computed contour FIGS. 4D, 4E, and 4F correspond to Fourier harmonics of 16, 32, and 64, respectively. These Figures show significantly better matching between boundary 414 and computed contour 416 in FIG. 4D, boundary 418 and computed contour 420 in FIG. 4E, and boundary 422 and computed contour 424 in FIG. 4F. In these successive figures, the computed contours that were grown with increasing numbers of Fourier harmonics become more defined compared to the boundaries. However, the incremental improvement is not overwhelmingly significant in evaluating the matches at FIGS. 4D, 4E and 4F. This also is indicated by the RMS values for FIGS. 4D to 4F being about the same. As such, there is not significant improvement by using 16, 32, or 64 Fourier harmonics although the match 4F, using 64 Fourier harmonics, visually appears to be the best match. It is to be noted, however, that if the number of harmonics is increased above a certain level past the optimum, the result will in fact deteriorate in the match.

b. Computed Contour Accuracy Versus Noise

FIGS. 5A, 5B, 5C, and 5D show a series of regions that have been evaluated for noise. More specifically, FIGS. 5A to 5D show a series of synthetic pictures in which the boundary (black) to be contoured is defined a priori by a fixed set of parameters p, which are identical to the set of parameters used in FIGS. 4A to 4F, and Gaussian distribution noise was added to the image. These images demonstrate the effect of noise on computed contour accuracy. Ten (10) Fourier harmonics are used for each of the figures. A comparison of the SNR (signal-to-noise ratio) and the RMS error for FIGS. 5A–5D is shown in Table 2:

TABLE 2

| Figure | SNR | RMS error |
|---|---|---|
| 5A | ∞ | 1.2 |
| 5B | 2.0 | 1.2 |
| 5C | 1.0 | 1.6 |
| 5D | 0.5 | 3.6 |

Figure 5A:
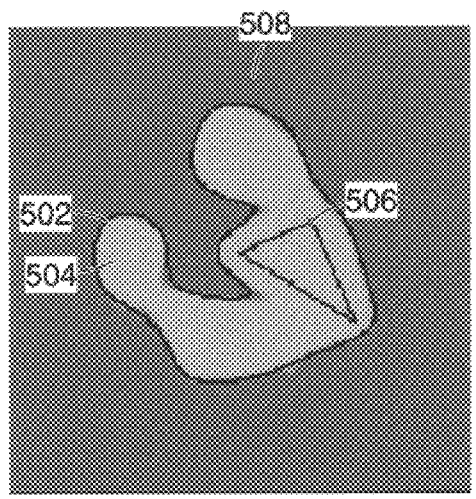
FIGS. 5A, 5B, 5C, and 5D show a series of synthetic pictures in which the boundary (black) to be contoured is defined a priori by a fixed set of parameters p, (as used in FIG. 4), and to which increasing levels of Gaussian noise has been added.

In FIG. 5A, boundary 502 defines ROI 504. Initial polygon 506 is found in ROI 504 to be grown to boundary 502. The success in growing polygon 506 is influenced by the clarity of the boundary between the ROI 504 and the area 508 outside ROI 504.

According to Table 2, in FIG. 5A the SNR is infinite. As is seen in reviewing FIG. 5A, there is a contrast between ROI 504 and area 508 outside boundary 502, but this high SNR also causes ROI 504 to have a significant gray-level value that is not desirable. This is true even though the RMS error is at a relatively low level.

Figure 5B:
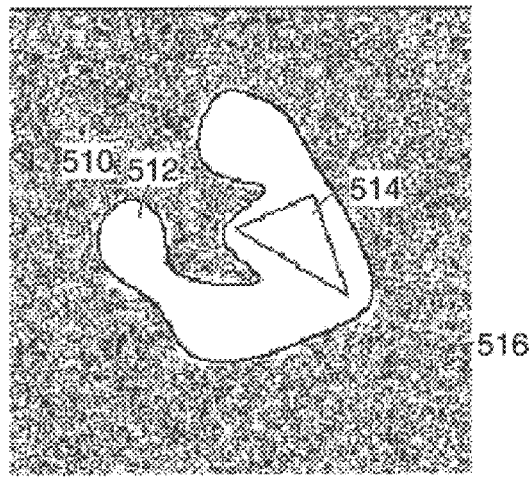

In FIG. 5B, boundary 510 defines ROI 512. Initial polygon 514 is formed in ROI 512. In FIG. 5B, the SNR is 2.0 and the RMS error has remained the same as it was when the SNR was infinite. In viewing FIG. 5B, it is seen that ROI 512 is in clear contrast to area 516 outside of ROI 512. This is a desirable situation to grow initial polygon 514 because this stark contrast will facilitate the growth to boundary 510 but not beyond it given the decision rules used by the present invention.

Figure 5C:
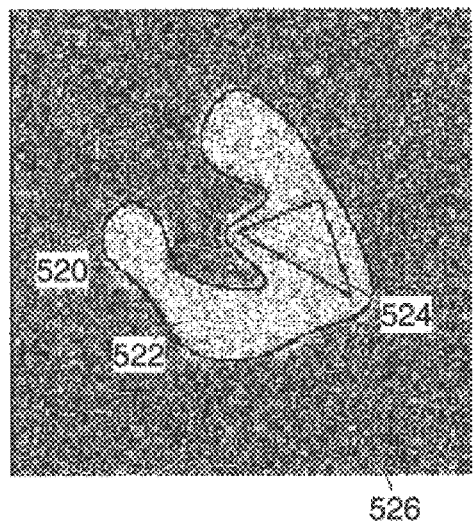
Figure 5D:
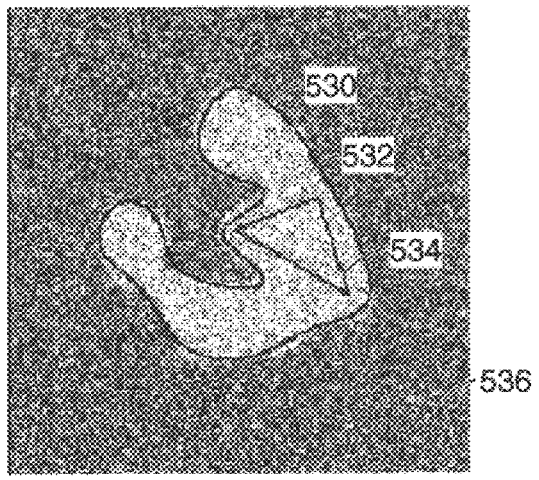

In FIG. 5C, boundary 520 defines ROI 502 and initial polygon 524 is formed in ROI 522. In FIG. 5D, boundary 530 defines ROI 532 and initial polygon 534 is formed in ROI 532. In FIG. 5C there is not a great amount of contrast between the gray-level values in ROI 522 and the area 526 outside of ROI 522. The same is true in FIG. 5D, there is not a great amount of contrast between the gray-level values in ROI 532 and the area 536 outside of ROI 532.

FIGS. 5C and 5D show situations in which the SNR is 1.0 and 0.5 respectively. It also is seen that the RMS error values have increased slightly when the SNR has decreased to 1.0, but increased significantly when the SNR has decreased to 0.5. These RMS error values are 1.6 to 3.6, respectively. In viewing FIGS. 5C and 5D, it is evident that as the SNR is decreased from 2.0 to 1.0 and 0.5, the difference between the gray-level values of pixels inside the ROI and outside the ROI is much less distinguishable. Therefore, after considering FIG. 5B, FIGS. 5C or 5D would not be desired environments for growing polygon to match the ROI boundary.

c. Automated Contouring of the Left Kidney from CT Images

FIGS. 6A, 6B, 6C, 6D, 6E, and 6F show a series of pictures of a section of left kidney 602. In FIGS. 6A to 6F, ten (10) Fourier harmonics were used.

FIG. 6A shows kidney 602 with interior inscribed (black polygon) 604. Polygon 604 is inscribed using interactive graphics. From inscribed polygon 604, the present invention was used to compute the contour (dashed) 606 to fit the boundary kidney 602.

FIGS. 6B to 6F show succeeding sections of left kidney 602 with significant variations in shape detail and interior textures. In each of these figures, the present invention was used to compute a contour that would fit the kidney section boundary. In FIG. 6B contour 606 was computed, in FIG. 6C contour 608 was computed, in FIG. 6D contour 610 was computed; in FIG. 6E contour 612 was computed; and in FIG. 6F contour 614 was computed.

The various kidney shapes and interior textures do not have any significant effect on the ability of the system and method of the present invention to compute the contours in FIGS. 6A–6F.

The terms and expressions which are used herein are used as terms of expression and not of limitation. There is no intention in the use of such terms and expressions of excluding the equivalents of the features shown and described, or portions thereof, it being recognized that various modifications are possible in the scope of the present invention.

What is claimed is:

1. A method for autocontouring a two-dimensional representation of a predetermined bounded object that may be part of an image created by a predetermined modality, with the image being defined by a plurality of pixels having property values representative of what is on the image, comprising the steps of:

(a) generating within the object an initial region of interest (ROI) with a boundary defined by a first supervised classifier based on properties of pixels inside the object compared with properties of pixels outside the object;

(b) generating a second supervised classifier based on the properties of pixels inside the ROI;

(c) expanding the ROI boundary using the second supervised classifier by evaluating the properties of a layer of pixels adjacent to a current exterior boundary of the ROI based on comparing pixel properties of each pixel in the current exterior layer to the properties of the pixels within the ROI, reclassifying the pixels in the current exterior layer as pixels to be included as part of the pixels within the ROI if the properties of discrete pixels in the current exterior layer substantially match in a predetermined manner the properties of the pixels within the ROI, and re-numerating the boundary of the ROI based on any reclassified pixels;

(d) generating a parametric representation of a contour based at least in part on two-dimensional coordinates of a predetermined number of points on the ROI boundary determined in step (c);

(e) generating an optimal objective function and a corresponding parametric contour;

(f) repeating steps (c)–(e) one exterior pixel layer at a time until a maximum match is captured;

(g) selecting a largest-valued optimal objective function that has been generated according to steps (e) and (f); and (h) creating a contour based of the objective function selected at step (g).

2. The method as recited in claim 1, wherein the predetermined modality generates contours in tomographic images.

3. The method as recited in claim 2, wherein the predetermined modality includes X-ray computed tomography (CT).

4. The method as recited in claim 2, wherein the predetermined modality includes magnetic resonance imaging (MRI).

5. The method as recited in claim 1, wherein the parametric representation is in a form of a finite Fourier series of two-dimensional coordinates that define the boundary of the ROI.

6. The method as recited in claim 5, wherein the finite Fourier series includes the use of a predetermined number of Fourier harmonics to minimize error between points the contour and points on the boundary of the ROI.

7. The method as recited in claim 6, wherein the number of Fourier harmonics relates to a length of the boundary.

8. A method for autocontouring a two-dimensional representation of a predetermined bounded object that may be part of an image created by a predetermined modality, with the image being defined by a plurality of pixels having property values representative of what is on the images, comprising the steps of:

(a) generating within the object an initial region of interest (ROI) with a boundary;

(b) generating a supervised classifier based on predetermined properties of pixels inside of the ROI and properties of pixels outside of the ROI for evaluating if pixels in a layer adjacent to a current exterior boundary of the ROI should be included as part of an interior of the ROI;

(c) expanding the boundary of the ROI using the supervised classifier by iteratively evaluating exterior layers of pixels adjacent to the boundary of the ROI until there is maximum matching of the ROI boundary and the object boundary; and (d) generating a contour for the object according to the maximum expanded ROI boundary based on a maximization of an objective function.

9. The method as recited in claim 8, wherein the predetermined modality generates contours in tomographic images.

10. The method as recited in claim 9, wherein predetermined modality includes X-ray computed tomography (CT).

11. The method as recited in claim 9, wherein predetermined modality includes magnetic resonance imaging (MRI).

12. A method for autocontouring a three-dimensional representation of a predetermined bounded object that may be part of an image created a series of two-dimensional images formed by a predetermined modality, with each of the two-dimensional images being defined by a plurality of pixels having property values representative of what is on the image, comprising the steps of:

(a) generating within an object on a single image an initial region of interest (ROI) with a boundary defined by a first supervised classifier based on properties of pixels inside the object on the single image compared with properties of pixels of with the same object in an adjacent image;

(b) generating a second supervised classifier based on the properties of pixels inside the ROI;

(c) expanding the ROI boundary using the second supervised classifier by evaluating the properties of a layer of pixels adjacent to a current exterior boundary of the ROI based on comparing pixel properties of each pixel of the current exterior layer to the properties of the pixels within the ROI, reclassifying the pixels in the current exterior layer as pixels to be included as part of the pixels within the ROI if the properties of discrete pixels in the current exterior layer substantially match in a predetermined manner the properties of the pixels within the ROI, and re-numerating the boundary of the ROI based on any reclassified pixels;

(d) generating a parametric representation of a contour based at least in part on two-dimensional coordinates of a predetermined number of points on the ROI boundary determined in step (c);

(e) generating an optimal objective function and a corresponding parametric contour, (f) repeating steps (c)–(e) one exterior pixel layer at a time until a maximum match is captured;

(g) selecting a largest-valued optimal objective function that has been generated according to steps (e) and (f);

(h) saving the objective function selected at step (g);

(i) repeating steps (a)–(h) for each two-dimensional image defining the three-dimensional representation of the object; and (j) creating a three-dimensional contour based of the objective functions selected and saved at steps (g) and (h).

13. The method as recited in claim 12, wherein the predetermined modality generates contours in tomographic images.

14. The method as recited in claim 13, wherein the predetermined modality includes X-ray computed tomography (CT).

15. The method as recited in claim 13, wherein the predetermined modality includes magnetic resonance imaging (MRI).

16. The method as recited in claim 12, wherein the parametric representation is in a form of a finite Fourier series of two-dimensional coordinates that define the boundary of the ROI.

17. The method as recited in claim 16, wherein the finite Fourier series includes the use of a predetermined number of Fourier harmonics to minimize error between points the contour and points on the boundary of the ROI.

18. The method as recited in claim 17, wherein the number of Fourier harmonics relates to a length of the boundary.

19. A method for autocontouring a three-dimensional representation of a predetermined bounded object that may be part of an image created a series of two-dimensional images formed by a predetermined modality, with each of the two-dimensional images being defined by a plurality of pixels having property values representative of what is on the image, comprising the steps of:

(a) generating within the object on a single image an initial region of interest (ROI) with a boundary;

(b) generating a supervised classifier based on predetermined properties of pixels inside of the ROI and properties of pixels outside of the ROI for evaluating if pixels in a layer adjacent to a current exterior boundary of the ROI should be included as part of an interior of the ROI;

(c) expanding the boundary of the ROI using the supervised classifier by iteratively evaluating exterior layers of pixels adjacent to the boundary of the ROI until there is maximum matching of the ROI boundary and the object boundary;

(d) generating an optimal objective function for the maximum matching ROI boundary;

(e) saving the optimal objective function generated at step (d);

(f) repeating steps (c)–(e) for each two-dimensional image defining the three-dimensional representation of the object; and (j) generating a three-dimensional set of contours based of the objective functions generated and saved at steps (d) and (e).

20. The method as recited in claim 19, wherein the predetermined modality generates contours in tomographic images.

21. The method as recited in claim 20, wherein the predetermined modality includes X-ray computed tomography (CT).

22. The method as recited in claim 9, wherein the predetermined modality includes magnetic resonance imaging (MRI).

* * * * *